United States Patent [19]

Murphy

[11] Patent Number: 4,873,379

[45] Date of Patent: Oct. 10, 1989

[54] PROCESS FOR MAKING 1,3-DIOLS FROM EPOXIDES

[75] Inventor: Mark A. Murphy, Corpus Christi, Tex.

[73] Assignee: Hoechst Celanese Corporation, Sommerville, N.J.

[21] Appl. No.: 198,364

[22] Filed: May 25, 1988

[51] Int. Cl.[4] .................... C07C 27/20; C07C 27/22; C07C 29/00

[52] U.S. Cl. .................................. 568/867; 568/865; 568/866

[58] Field of Search ................................ 568/483, 867

[56] References Cited

U.S. PATENT DOCUMENTS

| 3,054,813 | 9/1962 | Niederhauser | 568/426 |
|---|---|---|---|
| 3,463,819 | 8/1969 | Smith et al. | 568/483 |
| 3,687,981 | 8/1972 | Lawrence | 568/483 |
| 4,469,887 | 9/1984 | Brockhaus | 562/599 |

Primary Examiner—Werren B. Lone
Attorney, Agent, or Firm—Donald R. Cassady

[57] ABSTRACT

A process for manufacturing 1,3-glycols is disclosed. The process comprises reacting an epoxide with synthesis gas in the presence of rhodium in the presence of an alkali metal compound.

7 Claims, No Drawings

PROCESS FOR MAKING 1,3-DIOLS FROM EPOXIDES

BACKGROUND OF THE INVENTION

This invention relates to the manufacture of 1,3-diols from an epoxide. In one embodiment, this invention relates to the manufacture of 1,3-propanediol from ethylene oxide.

Glycols in general are valuable chemical compounds which find a wide variety of utilities. Such compounds are used, for example, as chemical intermediates in the manufacture of esters, as well as in the synthesis of polyesters. 1,3-propanediol (1,3-PDO), also referred to as 1,3-propylene glycol or trimethyleneglycol, in particular, had been found to be especially useful in a number of applications. Typically, 1,3-propanediol has been prepared by acid-catalyzed hydration of acrolein to form 3-hydroxypropanal which is subsequently hydrogenated to the corresponding glycol. The high cost of acrolein and the relatively low yields obtained in such reactions have not led to commercial processes for production of 1,3-propanediol which are cost competitive with other commercially available diols which in many instances can be substituted for 1,3-propanediol.

The preparation of 1,3-glycols by the hydroformylation of epoxides, utilizing phosphine-modified cobalt carbonyl complexes as the catalyst, is shown in U.S. Pat. No. 3,463,819. In particular, this patent shows the production of 1,3-propanediol by hydroformylation of ethylene oxide, using a tertiary phosphine-modified cobalt carbonyl catalyst. Although high yields (92%) of 1,3-propanediol were claimed to have been produced in diethyl ether solvent, catalyst concentrations were extremely high, the amount of ethylene oxide charged was low, and no indication of reaction times nor reaction rates was specified. This high catalyst concentration may have been necessary because of the limited catalyst turnover number i.e.; 2-4 moles of product/mole of cobalt and phosphine. Yields of 1,3-propanediol were substantially lower in solvents other than diethyl ether.

U.S. Pat. No. 3,687,981 is also directed to a process for manufacturing 1,3-propanediol. However, the process disclosed in the '981 patent employs two separate stages. In the first stage ethylene oxide undergoes a hydroformylation reaction to produce 2-(2-hydroxyethyl)-4-hydroxy-1,3-dioxane which is insoluble in the initial reaction solvent. The dioxane compound is separated from the initial reaction solvent and is subsequently catalytically hydrogenated to form trimethylene glycol. The patent generally discusses the possibility of using as the hydroformylation reaction catalyst, transition metals, particularly those of Group VIII of the Periodic Table, e.g., cobalt carbonyl tertiary phosphine and rhodium carbonyl. However, the examples in the said patent are limited to the use of dicobalt octacarbonyl catalyst.

U.S. Pat. No. 3,054,813 is directed toward a process for the production of 3-hydroxyaldehydes or alpha-beta unsaturated aldehydes by the reaction of epoxides with synthesis gas. Said patent shows the use of a cobalt carbonyl catalyst for the hydroformylation of ethylene oxide, but the product which resulted was acrolein.

In an article by Yokokawa et al., *Bulletin of the Chemical Society of Japan* (Vol. 37, page 677, 1964), there is shown an attempt to hydroformylate ethylene oxide and propylene oxide using a cobalt carbonyl catalyst. In the case of ethylene oxide, the product was overwhelmingly composed of acetaldehyde. Small amounts of acrolein were formed. In the case of propylene oxide, under some conditions reasonable yields of 3-hydroxybutyraldehyde were produced, but the production of 1,3-butanediol is not mentioned.

It is likely that processes which produce 1,3-glycols from epoxides using "hydroformylation" catalysts, produce 3-hydroxyaldehydes as chemical intermediates which can either be hydrogenated to 1,3-glycols in situ, or isolated in some manner (as in the form of the aforementioned hydroxyalkyldioxanes) and then hydrogenated in a separate step. However, 3-hydroxyaldehydes, such as 3-hydroxypropanal, are unusually reactive species and readily undergo a variety of side reactions. In a literature review entitled "New Synthesis with Carbon Monoxide", B Cornils, *Springer Verlag*, page 131, 1980, it Was stated that numerous attempts had been made to subject oxiranes (epoxides) to the hydroformylation reaction to produce hydroxyaldehydes and that on account of the greater reactivity, not only of epoxides, but also of the resulting hydroxyaldehydes, the epoxide hydroformylation generally led to the formation of a mixture of products and thus unsatisfactory yields.

Under the conditions of a hydroformylation reaction, isomerization of ethylene oxide to acetaldehyde (which is sometimes further hydrogenated to ethanol) can occur. Furthermore, if hydroformylation of ethylene oxide to 3-hydroxypropanal is successful, the 3-hydroxypropanal can dehydrate to yield acrolein, which can be hydrogenated to propanal or propanol, or the 3-hydroxypropanal can undergo condensation (aldol) reactions with other aldehyde molecules to give $C_6$ branched aldehydes, which can undergo dehydration and hydrogenation reactions. It is therefore highly desirable that a catalyst for the production of 1,3-propanediol from ethylene oxide should be able to rapidly hydrogenate 3-hydroxypropanal in situ before undesirable side reactions can occur. Such a catalyst would have the economic advantage of producing the 1,3-propanediol product in a single reactor, without the need for a large and expensive apparatus for the isolation and subsequent hydrogenation of aldehydes.

A one-step process for the manufacture of 1,3-PDO has recently been filed in the United States Patent and Trademark Office as application Serial No. 898,072; filed Aug. 20, 1986. According to that invention (1) an epoxide at a concentration from about 0.01 to about 30 wt. %; (2) rhodium at a molar concentration from about 0.00001 to about 0.1 molar; (3) a phosphine having the formula $$PR_1R_2R_3 \qquad \text{III}$$

wherein $R_1$, $R_2$, and $R_3$ are independently selected from the group consisting of aliphatic and aromatic hydrocarbon groups, the molar ratio of rhodium to phosphine being from about 10:1 to about 1:1; (4) water in an amount from about 0.00 to about 25 wt. % based on the weight of the reaction mixture; (5) CO; and (6) $H_2$; wherein the molar ratio of CO to $H_2$ is from about 10:1 to about 1:10, are caused to react at a temperature from about 50 to about 200° C. under a pressure from about 200 to about 10,000 psig, for a period of time which is sufficient to form at least some of the desired 1,3-glycol.

SUMMARY OF THE INVENTION

It has now been discovered that epoxides may be converted into 1,3-glycols by a hydrocarbonylation reaction which uses rhodium as the catalyst in the absence of the customary phosphine co-catalyst. Thus, the present invention provides a process for manufacturing 1,3-glycols of the formula

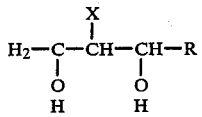

wherein R represents hydrogen, a monovalent aliphatic or aromatic group having from 1 to about 12 carbon atoms, or a divalent aliphatic group having from 4 to about 6 carbon atoms which together with X forms a cyclic structure, and X represents hydrogen, or if R is divalent, a bond with R. The process comprises reacting an epoxide of the formula

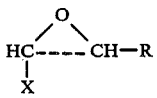

wherein R and X have the aforementioned meaning, with CO and $H_2$ in a suitable reaction solvent, wherein said process is characterized in that the reaction mixture contains (1) an epoxide of the foregoing structure at a concentration from about 0.01 to about 30 wt. % (2) rhodium at a molar concentration from about 0.00001 to about 0.1 molar; (3) an alkali metal compound in a concentration of from about 0.00001 molar to about 0.1 molar, typically the salt to rhodium ratio is from about 5:1 to 1:5; (4) water in an amount from about 0.00 to about 25 wt. % based on the weight of the reaction mixture; (5) CO; and (6) $H_2$; wherein the molar ratio of CO to $H_2$ is from about 5:1 to about 1:5; wherein the reaction takes place at a temperature from about 50 to about 200° C. under a pressure from about 200 to about 10,000 psig, for a period of time which is sufficient to form at least some of the desired 1,3-glycol.

DETAILED DESCRIPTION OF THE PREFERRED EMBODIMENTS

As indicated above, the process of the present invention provides a method for the manufacture of 1,3-glycols through the hydrocarbonylation of epoxides. The desired glycols therefore contain one more carbon atom and one more oxygen atom than the epoxide. Thus, for example, when the epoxide reactant is ethylene oxide, containing 2 carbon atoms, the resultant 1,3-glycol is 1,3-propanediol, containing 3 carbon atoms. Examples of other specific epoxides which are useful in the present invention include propylene oxide, 1,2-epoxyoctane, cyclohexene oxide, and styrene oxide.

The epoxides, as indicated previously, have the general formula

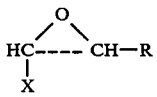

wherein R is hydrogen, a monvalent aliphatic or aromatic group having from 1 to about 12 carbon atoms, or a divalent aliphatic group having from 4 to about 6 carbon atoms which together with X forms a cyclic structure, and X represents hydrogen or, if R is divalent, a bond with R. R therefore may be a monovalent alkyl group containing, for example, from 1 to 6 carbon atoms or may be a divalent alkyl group or an aromatic group, such as a phenyl group. If, for example, R is a divalent alkyl group having 4 carbon atoms, then the epoxide is cyclohexene oxide. The epoxide is usually present in the reaction mixture at a concentration of about 0.01 to about 30 wt. %. Typically the concentration of epoxide is from about 0.5 to 20 wt. %.

The various epoxides may require different reaction conditions, to achieve optimum results in terms of product yield and selectivity, as well as different specific rhodium and alkali metal ion, components in the reaction medium.

The carbonylation reaction, as indicated previously, takes place in a suitable solvent or mixture thereof. As a general principle, solvents which may be categorized as having medium to high polarity are suitable, such as aromatic solvents, ethers, polyethers, amides, sulfones, and alcohols. Depending upon the reactivity of the particular solvent selected and the specific conditions to be employed, ketones, and esters may also be usable. The preferred solvents generally are high molecular weight ethers, polyethers, and cyclic ethers, especially glycol polyethers. An especially preferred solvent is tetraglyme, the dimethylether of tetraethylene glycol, 2,5,8,11,14-pentaoxapentadecane. Particularly useful solvents also include tetrahydrofuran, diglyme, and Ucon TM oils which are mixed glycol polyethers of ethylene and propylene glycol subunits.

To be suitable, a solvent should solubilize the catalyst and promoters and the epoxide reactant. Preferred solvents should not substantially react with any of the components of the reaction mixture or the desired product. Thus, for lower molecular weight epoxides and glycols, solvents such as tetraglyme, tetrahydrofuran and the like are usually used. For higher molecular weight epoxides and glycols, hydrocarbon solvents such as petroleum ethers, toluene, and xylene may be appropriate. The latter solvents are less suitable for lower molecular weight epoxides and glycols such as ethylene oxide and 1,3-propanediol.

The rhodium which is employed in the present process may be introduced in the form of rhodium metal, rhodium salts, and/or rhodium complexes. The only proviso is that the rhodium complex should not contain ligands which insolubilize or poison the catalyst. Thus, selection of the particular rhodium component may, in part, depend upon the solubility of the particular rhodium metal or compound in the specific solvent utilized as the reaction medium. The rhodium useful in the practice of the present invention includes rhodium metal, rhodium oxides, $RhI_3$, $RhBr_3$, $RhCl_3$, $Rh(Acac)_3$, $Rh(CO)_2Acac$, $Rh_6(CO)_{16}$, $[RhCl(CO)_2]_2$ and $Rh(NO_3)_3$, wherein Acac represents acetylacetonate. Likewise Rhodium may be used as a pre-formed anion, as for example $Rh_6(CO)_{15}{}^{2-}$ and other similar anionic rhodium cluster salts.

The concentration of the rhodium in the reaction solvent should be in the range from about 0.00001 molar to about 0.1 molar. Preferably, the concentration of rhodium will be from about 0.005 to about 0.1 molar.

Acids can be added to the reaction mixture and are particularly useful if the pH of the reaction mixture is on the basic side of neutral.

Usually medium or strong acids are preferable for use in the present process. Some acids are, however, less desirable because of their corrosive nature or due to their insolubility in the particular solvent. Hydrogen iodide and hydrogen chloride have been found to be extremely useful acids in the process.

Preferable acids include phosphoric acid, methane sulfonic, and p-toluene sulfonic acid. Weaker acids such as acetic may be operable, depending upon the particular operating conditions, but may also become esterified under the conditions of the reaction. Suitable acids for the process of this invention include such strong acids as nitric acid, phosphoric acid, hydriodic acid, hydrochloric acid, hydrobromic acid, p-toluene sulfonic acid, and the like. Weak acids suitable for the process include benzoic acid, acetic acid, propionic acid, and the like.

Promoter concentrations are not particularly critical to the rate or to the yield of 1,3-diol with the alkali metal ion to Rh ratio being typically from about 10:1 to about 1:5. Cations may include $Li^+$, $Na^+$, $K^+$, $Rb^+$, and $Cs^+$. The anions comprising the promoter must be a solubilizing anions in the solvent under the conditions of the reaction. Typical anions may include $F^-$, $CL^-$, $Br^-$, $I^-$, $NO_3^-$, $OH$, benzoate, acetate, sulfonate, and the like.

The ratio of hydrogen to carbon monoxide employed in the hydrocarbonylation reaction should be equal to or greater than 1:1 and preferably no greater than about 5:1, although acceptable yields are realized at concentrations in narrow ranges on both sides of the preferred range.

With respect to the pressure employed during the hydrocarbonylation reaction, the pressure is not critical and generally falls within the range from about 200 to about 10,000 psig. Preferably, the pressure falls in the range of from about 1,000 to about 4,000 psig.

The temperature used in the carbonylation reaction also is not critical. As a general proposition, it has been found that increasing temperature also increases rates. However, increasing temperatures may have an adverse affect on selectivity. Thus, some balancing of temperature is required in order to achieve suitable rates and suitable selectivities. Generally, a temperature of from about 50 to about 200° C. will be employed, preferably from about 100 to about 150° C. composition, reaction pressure, and reaction temperature, all will vary somewhat based upon the particular reaction conditions employed and adjustment thereof is within the ordinary skill of one in the art.

Water, in general, has been found to be useful in conjunction with many catalysts and solvents. In particular, though the presence of water is not necessary for the function of the catalysts used in this invention, in the absence of water, substantial induction periods are sometimes observed between the injection of ethylene oxide and the onset of the uptake of synthesis gas and the production of product, such as 1,3propanediol. It has been found that the presence of small amounts of water can sometimes substantially decrease the length of the induction periods, and hence shorten the overall reaction times. However, if the amount of water is increased beyond a given level, poorer yields may result. As a broad proposition, from about 0.00 to about 25 wt. % water is employed, preferably from about 0.0 to about 10 wt. %. The amount of water employed, as indicated, to achieve optimum results, will vary depending upon the particular reaction system and conditions employed.

The present invention is capable of achieving yields of 1,3- glycols, such as 1,3-propanediol in about 70 % yield based upon the epoxide, such as ethylene oxide, and production rates of substantially about 1 mole/liter/hour in a single carbonylation reactor. Such results are certainly unexpected and surprising, since the use of rhodium catalysts for the carbonylation of epoxides to 1,3-glycols without the presence of phosphine ligands in the reaction mixture has not been shown in the prior art. The present results ar also surprising in view of the fact that most prior art cobalt catalysts generally only achieved substantially lower rates and efficiencies for precursors of 1,3-propanediol, while the present process provides a high yields, single-step process for the production of 1,3-glycols without the need for separate, large hydrogenation reactors for 1,3-glycols precursors.

The present invention is further shown by the following non-limiting examples.

GENERAL EXPERIMENTAL METHOD EMPLOYED IN THE EXAMPLES

All examples were performed in a batch autoclave unit which consisted of a 300 cc Hastelloy autoclave equipped with remotely operable controls for feeds, vents, stirring, heating, cooling, and the like. Standard stainless-steel tubing and Swagelok fittings were employed at the lower reactor pressures. At pressures of 2500 psig, high-pressure type fittings, valves, and tubings were employed.

All catalysts and solvents were weighed under nitrogen and rapidly charged to a cold autoclave which was then purged twice with nitrogen and twice with synthesis gas. Subsequently, the autoclave was pressurized with synthesis gas to the desired pressure and heated under slow stirring to reaction temperature, over a period of 0.5 to 4.0 hours. Ethylene oxide was then injected into the autoclave from either a pressurized blowcase bomb or a Ruska syringe pump, at which time fast stirring was commenced and the total reactor pressure raised to the final desired value, using synthesis gas to control the pressure. Constant reactor pressures were maintained automatically during the runs by feeding synthesis gas on demand from a high-pressure synthesis gas reservoir of known volume. The uptake of reaction synthesis gas wa monitored by periodic measurement of the pressure of the synthesis gas reservoir. Runs were terminated, usually when synthesis gas uptake slowed to nearly 0, by slowing the stirring rate, terminating the synthesis gas feed, and cooling the reactor as rapidly as possible, typically over a 30 to 60 minute period.

Small quantities of ethylene oxide were injected into the reactor which was hot and pressurized, using either a Ruska syringe or a pressurized blowcase bomb by condensation of ethylene oxide vapor, from a lecture bottle, into the blowcase bomb which was chilled to dry ice temperatures. When ethylene oxide had been charged to the blowcase bomb; the blowcase bomb was detached from the transfer apparatus, weighed, then .connected to the autoclave.

When the Ruska pump method was used for injecting the ethylene oxide, liquid ethylene oxide was transferred through stainless steel lines to the Ruska syringe pump which then injected the ethylene oxide into the autoclave unit.

Because liquid ethylene oxide became held up in the lines, fittings, and valves leading to the autoclave, it was necessary to charge somewhat larger than theoretical quantities of ethylene oxide to the blowcase bomb or Ruska pump and then calibrate the unit for the quantity of ethylene oxide which actually reached the autoclave. Calibration runs were performed by charging the reactor with 100 grams of water and 1.8 grams of sulfuric acid and heating it to 100° C. Ethylene oxide was then charged to the blowcase bomb or Ruska pump, injected into the reactor, which was then heated for two hours to achieve ethylene oxide hydrolysis to ethylene glycol. The resulting ethylene glycol:water solutions were analyze for ethylene glycol using gas chromatography. In a typical run, 12.0 grams of ethylene oxide would be charged to the blowcase bomb and the ethylene glycol equivalent of 10.0 grams of ethylene oxide reached the reactor. Ethylene oxide feed was then back-calculated from the ethylene glycol and plots of ethylene oxide observed versus ethylene oxide charged, were constructed. Such plots were found to be reasonably linear over the range of 5 to 15 grams of ethylene oxide and typically showed 75 to 85% ethylene oxide efficiency in the transfer operation. The results of such calibration runs were then used to calculate ethylene oxide feed for the catalytic carbonylation runs.

With respect to the materials employed in the Examples, the alkali metal compounds were purchased from Alfa Products. $Rh(CO)_2Acac$ was either purchased from Englehard or prepared from $RhCl_3 \cdot 3H_2O$, acetylacetone, and dimethylformamide and then recrystallized from hexane to yield green-red crystalline needles.

Ethylene oxide (99.7% min) was purchased from Matheson and stored in chilled water. $H_2/CO$ mixtures were purchased from Iweco. Tetraglyme was used in the Examples as received from Aldrich, and was vacuum distilled from $Ca/H_2$.

In the following examples where yields are quoted, yields were calculated by dividing the moles of product obtained by the moles of EO charged (via use of the EO calibration procedure) to the reactor.

The following examples demonstrate the use of varying concentrations of metal ion salts on the reaction.

Eighty grams of tetraglyme, 1.05 grams of water, 0.52 gram of $Rh(CO)_2Acac$, and the indicated amount (mole per mole of Rh) of lithium salt were charged into an autoclave according to the standard procedure. The mixture was pressurized to 2000 psig with 2:1 $H_2/CO$ syn gas at ambient room temperature and then quickly heated to 110° C. The resultant mixture was held at this condition (110° C. and 2300 psig) for about 1.5 hours. Twelve and three-tenths grams of ethylene oxide was pressurized into the reaction from the Ruska pump and the total pressure increased to 2500 psig with 2:1 $H_2/CO$ to initiate the reaction. Gas uptake usually began immediately and the heat evolution from the reaction necessitated the use of a cooling water coil to maintain the indicated reaction temperature. After gas uptake was complete, the reaction was quenched and the products analyzed.

| LiI (eq/eqRh) | 1,3-PDO yield % (mole per mole EO) |
| --- | --- |
| 0.5 | 44.1 |
| 2.0 | 46.9 |
| 4.0 | 46.0 |
| Li(acetate) (eq/eqRh) | |
| 0.5 | 48.4 |
| 1.0 | 55.4 |
| 2.0 | 51.1 |
| 4.0 | 48.0 |

EXAMPLE 2

The procedure of Example 1 was repeated using cesium compounds.

| CsI (eq/eqRh) | 1,3 PDO yield % (mole per mole EO) |
| --- | --- |
| 0.5 | 63.0 |
| 4.0 | 9.7 |
| Cs(acetate) (eq/eqRh) | |
| 0.1 | 0.0 |
| 0.3 | 13.3 |
| 0.4 | 34.5 |
| 0.5 | 68.7, 56.3, 57.5 |
| 0.6 | 58.7 |
| 0.74 | 19.7* |
| 0.74 | 45.5* |
| 0.75 | 58.9 |
| 0.9 | 27.0 |
| 1.0 | 15.2 |
| 1.5 | 2.1 |
| 4.0 | 2.7 |
| Cs(Acetate) + $H_3PO_4$ (1:1:1) | 5.7 |
| CsCl | |
| 4.3 | |
| 0.5 | 61.6 |
| 0.75 | 69.8 |
| 1.0 | 43.1, 36.8 |
| 1.5 | 16.0 |
| CsOH (eq/eq Rh) | |
| 0.75 | 22.5 |

*Cs(Acetate) was hydrated and dissolved in the reaction mixture. Stoichiometry unknown.

The following example demonstrates the effort of varying pressure in the reaction.

EXAMPLE 3

The procedure of Example I was repeated using cesium acetate at a concentration of 0.5 eq/eqRh and the indicated pressure.

| Pressure (psig) | 1,3 PDO yield % (mole per mole EO) |
| --- | --- |
| 1400 | 42.2 |
| 2500 | 68.7, 56.3, 57.5 (from Ex. 2) |
| 3500 | 67.8 |

The following example demonstrates the effect of varying temperature in the reaction.

EXAMPLE 4

The procedure of Example 1 was repeated using cesium acetate at a concentration of 0.5 eq/eqRh and the indicated temperature:

| Temperature °C. | 1,3-PDO Yield % (moles per mole EO) |
| --- | --- |
| 110 | 68.7, 56.3, 57.5 (from Ex. 2) |
| 120 | 63.8 |
| 130 | 68.4 |
| 140 | 54.6 |

The following example illustrates the effect of varying the solvent o the yield.

EXAMPLE 5

The method of Example 1 was repeated using as a catalyst 0.5 moles of cesium acetate salt per mole of Rh catalyst [Rh(CO)$_2$Acac] and 1.0 g of water in varying solvent systems. The reaction was performed in the usual manner at 110° C. and 2500 psig.

| Solvent | 1,3-PDO Yield % (moles per mole EO) |
|---|---|
| Tetraglyme | 68.7, 56.3, 57.5 |
| Ucon 50-HB-100 | 37.3, 47.4 |
| Sulfolane (Tetrahydrothiophene 1,1-dioxide) | 4.8 |
| 12.5% Sulfolane, 87.5% Tetraglyme | 58.7 |

The following examples demonstrate the use of the blowcase bomb transfer device to add ingredients to the reaction mixture.

EXAMPLE 6

Eighty grams of tetraglyme, 1.07 grams of water, 2 mMole (0.52 grams) of Rh(CO)$_2$Acac, and 2 mMoles of lithium ethyleneglycolate (0.138 grams) were charged into an autoclave and heated to 110° C. under 2300 psig of 2:1 H$_2$/CO. Ethylene oxide (12.6 grams) was injected from a blowcase bomb, and the pressure increased to 2500 psig. Gas uptake began after 15 minutes and the run was terminated after 20 hours. Analysis of the product showed a yield (moles per mole of EO) of 47.77%.

EXAMPLE 7

The method of Example 5 was followed except that a mixture of 8 mMoles LiI and 2 mMoles Li(acetate) was used as the salt component. The yield of 1,3-PDO was 33.60%.

EXAMPLE 8

The method of Example 5 was followed except that 8 mMoles of LiI was used as the salt component. The yield of 1,3-PDO was 36.88%.

The following examples demonstrate the effect of adding an acid to the reaction mixture.

EXAMPLE 9

The method of Example 7 was followed except that 2 mMoles of HI was added to the reaction mixture. The yield of 1,3-PDO was 31.60%.

EXAMPLE 10

The method of Example 7 was followed except that 1.7 mMoles of phosphoric acid was added to the reaction mixture. The yield of 1,3-PDO was 32.12%.

COMPARATIVE EXAMPLES

Eighty grams of tetraglyme, 1.05 grams of water, 0.52 grams of Rh(CO)$_2$Acac, and the indicated amount of promoter (mole per mole of Rh) were charged into an autoclave in the usual manner. The mixture was pressurized to 2000 psig with 2:1 H$_2$/CO syn gas at ambient room temperature, heated to 110° C., and held at 110° C. for about 1.5 hours. Twelve and three-tenths grams of ethylene oxide were pressurized into the reaction from the Ruska pump and the total pressure increased to 2500 psig with 2:1 H$_2$/CO to initiate the reaction.

Gas uptake was noted and the reaction was terminated after any gas uptake was complete.

| Catalyst (Promoter) | 1,3-PDO Yield % (mole per mole EO) |
|---|---|
| Mg (acetate)$_2$ | 0 |
| Zn (acetate)$_2$ | 0 |
| Cu (acetate) | 0 |
| Mg (formate)$_2$ | 0 |
| Sr (OH)$_2$ | 0 |

What is claimed is:

1. A single-step process for manufacturing 1,3-propanediol from ethylene oxide with CO and H$_2$ in an ether reaction solvent, said process being characterized by reacting a reaction mixture comprising (1) ethylene oxide at a concentration from about 0.01 to about 30wt. %; (2) rhodium at a molar concentration from about 0.00001 to about 0.1 molar; (3) an alkali metal compound in a concentration of from about 0.00001 molar to about 0.1 molar; (4) water in an amount up to about 25 wt. % based on the weight of the reaction mixture; (5) CO; and (6) H$_2$; wherein the molar ratio of CO to H$_2$ is from about 1:1 to about 1:5, and wherein the reaction takes place at a temperature from about 50° to about 200° C. under a pressure from about 200 to about 10,000 psig, for a period of time which is sufficient to form 1,3-propanediol.

2. The process of claim 1 wherein the alkali metal compound is a member of the group consisting of lithium iodide, lithium acetate, lithium chloride, lithium ethyleneglycolate, cesium chloride, cesium acetate, and cesium iodide.

3. The process of claim 1 wherein the alkali metal ion to rhodium ratio is from about 10:1 to about 1:5.

4. The process of claim 1 wherein the solvent is selected from the group consisting of tetraglyme, tetrahydrofuran, and a mixture of glycol polyethers of ethylene and propylene glycols.

5. The process of claim 1 wherein the rhodium is selected from the group consisting of rhodium metal, rhodium oxides, RhI$_3$, RhBr$_3$, RhCl$_3$, Rh(Acac)$_3$, Rh(CO)$_2$Acac, Rh$_6$(CO)$_{16}$, [RhCl(CO)$_2$]$_2$, and Rh(NO$_3$)$_3$.

6. The process of claim 5 wherein the rhodium is present at a concentration from about 0.005 to about 0.10 molar.

7. The process of claim 1 wherein the pressure is from about 1000 t o about 3000 psig and the temperature is from about 100° to about 150° C.

* * * * *